United States Patent
Rendenbach-Mueller et al.

[11] Patent Number: 5,424,312
[45] Date of Patent: Jun. 13, 1995

[54] AMINOALKYL-SUBSTITUTED 2-AMINO-1,3,4-THIADIAZOLES, THE PREPARATION AND USE THEREOF

[75] Inventors: Beatrice Rendenbach-Mueller, Waldsee; Liliane Unger, Ludwigshafen; Hans-Juergen Teschendorf, Dudenhofen, all of Germany

[73] Assignee: BASF Aktiengesellschaft, Ludwigshafen, Germany

[21] Appl. No.: 162,115

[22] PCT Filed: May 11, 1992

[86] PCT No.: PCT/EP92/01028
§ 371 Date: Dec. 13, 1993
§ 102(e) Date: Dec. 13, 1993

[87] PCT Pub. No.: WO92/22541
PCT Pub. Date: Dec. 23, 1992

[30] Foreign Application Priority Data
Jun. 15, 1991 [DE] Germany .................. 41 19 755.0

[51] Int. Cl.⁶ .................. C07D 285/135; A61K 31/41
[52] U.S. Cl. .................. 514/252; 514/256; 514/318; 514/326; 514/333; 544/245; 544/367; 546/193; 546/209; 546/277
[58] Field of Search .................. 546/193, 209, 277; 544/295, 367; 514/252, 256, 318, 376, 333

[56] References Cited

U.S. PATENT DOCUMENTS
4,642,132 2/1987 Schirmer .................. 548/138

FOREIGN PATENT DOCUMENTS
1053085 12/1966 United Kingdom .

*Primary Examiner*—Robert Gerstl
*Attorney, Agent, or Firm*—Keil & Weinkauf

[57] ABSTRACT

Aminoalkyl-substituted 2-amino-1,3,4-thiadiazoles of the formula

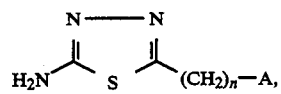

where n and A have the meanings stated in the description, and the preparation thereof are described. The compounds are suitable for controlling diseases.

5 Claims, No Drawings

AMINOALKYL-SUBSTITUTED 2-AMINO-1,3,4-THIADIAZOLES, THE PREPARATION AND USE THEREOF

This application is 371 PCT/EP92/01028 filed May 11, 1992.

The present invention relates to aminoalkyl-substituted 2-amino-1,3,4-thiadiazoles, the preparation thereof and the use thereof for controlling diseases.

GB 1 053 085 describes aminoalkylthiadiazoles which have antitussive, analgesic, antipyretic and hypoglycemic effects.

We have now found that aminoalkyl-substituted 2-amino-1,3,4-thiadiazole derivatives of the formula I

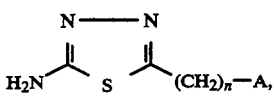

where
n is an integer from 2 to 6, and
A is

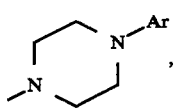

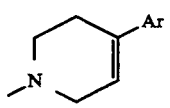

or

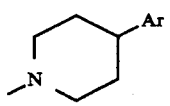

where Ar is phenyl which is unsubstituted or monosubstituted by $C_1$-$C_5$-alkyl, $C_1$-$C_5$-alkoxy, halogen, nitro, hydroxyl, trifluoromethyl or cyano, or is pyridyl, pyrimidinyl or thienyl, and the salts thereof with physiologically tolerated acids have interesting pharmacological properties.

A in the formula I is preferably

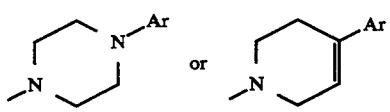

where Ar is unsubstituted phenyl, pyridyl or pyrimidinyl, and n is preferably 2, 3 or 4.

The compounds of the formula I can be prepared by
a) reacting an ω-X-alkylthiadiazole of the formula II

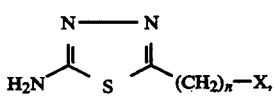

where n is as defined above, and X is a leaving group such as chlorine, bromine or $RSO_2O$—[R=-$C_1$-$C_4$-alkyl or phenyl which is unsubstituted or substituted by $C_1$-$C_3$-alkyl or halogen], or a hydrohalide of this compound, with an amine of the formula III $$HA \qquad\qquad III,$$

where A has the stated meanings, or
b) reacting an ω-amino carboxylic acid of the formula IV $$HO_2C\text{—}(CH_2)_n\text{—}A \qquad\qquad IV,$$

where A and n are as defined above, with thiosemicarbazide,
and, where appropriate, converting the resulting compounds into their salts with physiologically tolerated acids.

The reactions in process a) take place in the melt, if required also in the presence of a solvent, e.g. ethyl acetate, tetrahydrofuran, dimethylformamide, dimethoxyethane, toluene or xylene, at from room temperature to the boiling point of the solvent, preferably in the presence of a base such as sodium methylate, sodium ethylate, sodium hydride, sodium carbonate, potassium carbonate, or of an amine, e.g. pyridine. It is also possible where appropriate for the amine component IV in excess to act as reagent, base and solvent.

The ω-X-alkylthiadiazoles of the formula II used as starting materials can be prepared, for example, by reacting ω-X-substituted carboxylic acids of the formula V $$HO_2C\text{—}(CH_2)_n\text{—}X \qquad\qquad V,$$

where n and X have the stated meanings, with thiosemicarbazide. The carboxylic acids of the formula V are mostly known from the literature or can be prepared by known methods.

The reaction in process b) takes place in the presence of a diluent or solvent, preferably a strong acid, for example concentrated sulfuric acid, and expediently at from room temperature to the boiling point of the solvent. The reaction is generally complete in from 1 to 6 hours, depending on the precursors. The reaction product can be isolated and purified in conventional ways. The ω-amino carboxylic acids of the formula IV used as starting materials are known in some cases, or they can be prepared in a conventional way by reacting the ω-substituted carboxylic acids of the formula V with amines of the formula III.

The resulting compounds according to the invention are, where appropriate, converted into their addition salts with physiologically tolerated acids. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid and benzoic acid. Others are to be found in Fortschritte der Arzneimittelforschung, Vol. 10, pp. 224 et seq., Birkhäuser Verlag, Basel and Stuttgart, 1966.

The acid addition salts are usually obtained in a conventional way by mixing the free base or solutions thereof with the appropriate acid or solutions thereof in an organic solvent, for example a lower alcohol such as methanol, ethanol or propanol, a halohydrocarbon such as methylene chloride, an ether such as methyl t-butyl ether or diisopropyl ether, a ketone such as acetone or butanone or an ester such as ethyl acetate. It is also possible to use mixtures of the said solvents to improve crystallization. In addition, pharmaceutically acceptable aqueous solutions of acid addition compounds of the compounds I according to the invention can be prepared by dissolving the free bases in an aqueous acid solution.

The compounds according to the invention are suitable for controlling diseases, especially for treating disorders of the central nervous system (e.g. parkinsonism, schizophrenia) and high blood pressure. They have, in particular, valuable properties as dopamine recepters in some cases with selectivity for presynaptic dopamine receptors, or as dopamine antagonists. The compounds of the formula I show affinity for the dopamine receptor in receptor binding assays; they inhibit motility in mice (measured in cages with a photoelectric beam) and influence the pivoting behavior of rats with unilateral 6-hydroxydopamine lesions of the substantial nigra (Brain Research 24, (1970) 485–493).

The effects of the novel compounds can be shown in the receptor binding assay as follows:

Striata from rats (Sprague Dawley, Charles River) were homogenized immediately after removal in 0.32M sucrose solution (0° C.). The homogenate was filtered through gauze, the filtrate was centrifuged at 1000×g (5 min at 4° C.) and the resulting supernatant was centrifuged at 40000×g (4C 10 min) The residue (membranes) was taken up in incubation buffer (50 mM tris-HCl, 1 mM $MgCl_2$ and 0.1% ascorbic acid, pH 7.4) and incubated at 37° C. for 20 min. The residue was subsequently washed 2× with incubation buffer by resuspension and recentrifugation. The membranes were frozen in portions in liquid nitrogen.

The assay mixtures (1 ml) were composed of membranes (380 μg of protein), 1 nM $^3$H-ADTN (NEN, Dreieich Germany, specific radioactivity 1.4 TBq/mmol) and 0.1 μM SCH 23390 (total binding) or a) with the addition of 50 nM spiperone (non-specific binding) or b) with test substance. The mixtures were prepared in triplicate.

After the incubation (40 min at 25° C.) the mixtures were filtered through glass fiber filters (Whatman GF/B) and briefly washed with ice-cold washing buffer (tris-HCl, pH 7.4). The radioactivity retained on the filters was determined by liquid scintillation counting. The non-specific binding comprised about 40-50% of the total binding.

The evaluation of the competition plots and the determination of the dissociation constant took place by iterative non-linear regression analysis based on the "ligand" program (Muson and Rodbard: Anal. Biochem. 107 (1980) 220).

Affinity of the test substances for the dopamine $D_2$ receptor

| Example | Ki (nM) |
| --- | --- |
| 4 | 30 |
| 7 | 30 |
| 10 | 32 |
| 18 | 5 |
| 19 | 10 |
| 21 | 44 |
| 24 | 37 |

The compounds according to the invention can be administered orally or parenterally (subcutaneously, intravenously, intramuscularly, intraperitoneally) in a conventional way. Administration can also take place through the nasopharyngeal space using vapors or sprays.

The dosage depends on the age, condition and weight of the patient and on the mode of administration. The dose of active substance is, as a rule, about 10–500 mg per patient and day on oral administration and about 1–100 mg per patient and day on parenteral administration.

The novel compounds can be used in the conventional solid or liquid pharmaceutical forms, e.g. as uncoated or (film-) coated tablets, capsules, powders, granules, suppositories, solutions or sprays. These are produced in a conventional way. The active substances can be processed with conventional pharmaceutical aids such as tablet binders, fillers, preservatives, tablet disintegrants, flow regulators, plasticizers, wetting agents, dispersants, emulsifiers, solvents, retarding agents, antioxidants and/or propellant gases (cf. H. Sucker et al.: Pharmazeutische Technologie, Thieme-Verlag, Stuttgart, 1978). The pharmaceutical forms obtained in this way normally contain the active substance in an amount of from 1 to 99% by weight.

The following Examples illustrate the invention:

EXAMPLE 1

2-Amino-5-[2-(4-phenylpiperazinyl)ethyl]-1,3,4-thiadiazole dihydrochloride 4.5 g of 2-amino-5-(2-chloroethyl)-1,3,4-thiadiazole, 8.9 g of 4-phenylpiperazine and 0.2 g of sodium iodide in 70 ml of toluene were heated at 80° C. for 4 h. 3.8 ml of triethylamine were added and the mixture was then stirred at this temperature for a further 5 h and cooled to RT, and the resulting solid was filtered off with suction and partitioned between methylene chloride and 2N HCl. The aqueous phase was separated off and made alkaline with 5N NaOH. The solid which precipitated at pH 6–7 was filtered off with suction, washed with water and acetone and taken up in ethanol, and ethereal HCl was added. The crystals were filtered off with suction and dried under reduced pressure.

Yield: 2.5 g (25%) Melting point 186°–188° C.

The following were prepared as in Example 1:

2. 2-Amino-5-[2-(4-pyrimid-2-ylpiperazinyl)ethyl]-1,3,4-thiadiazole trihydrochloride Yield: 27% Melting point 148° C. (decomposition)

3. 2-Amino-5-[2-(4-phenylpiperidinyl)ethyl]-1,3,4-thiadiazole dihydrochloride

Yield: 54% Melting point 178°–181° C.

4. 2-Amino-5-[2-(1,2,3,6-tetrahydro-4-phenylpyridyl)ethyl]-1,3,4-thiadiazole hydrochloride Yield: 79% Melting point 183°–184° C.

5. 2-Amino-5-[2-(4-pyrimidin-2-ylpiperazinyl)ethyl]-1,3,4-thiadiazole hydrochloride Yield: 22% Melting point 140° C. (decomposition)

6. 2-Amino-5-[2-(4-methoxyphenyl)-piperazinyl)ethyl]-1,3,4-thiadiazole hydrochloride Yield: 31% Melting point 180° C. (decomposition)

7. 2-Amino-5-[2-(4-(4-chlorophenyl)-1,2,3,6-tetrahydropyridyl)ethyl]-1,3,4-thiadiazole dihydrochloride Yield: 20% Melting point 154° C. (decomposition)

8. 2-Amino-5-[2-(4-(2-fluorophenyl)piperazinyl)ethyl]-1,3,4-thiadiazole hydrochloride Yield: 27% Melting point 187°–189° C.

9. 2-Amino-5-[3-(4-phenylpiperidinyl)propyl]-1,3,4-thiadiazole hydrochloride

Yield: 20% Melting point 225°–226° C.

10. 2-Amino-5-[3-(1,2,3,6-tetrahydro-4-phenylpyridyl)-propyl]-1,3,4-thiadiazole hydrochloride
   Yield: 17% Melting point 170°–172° C.
10. 2-Amino-5-[3-(4-(2-fluorophenyl)piperazinyl)-propyl]-1,3,4-thiadiazole hydrochloride
   Yield: 22% Melting point 165°–166° C.
12. 2-Amino-5-[3-(4-phenylpiperazinyl)propyl]-1,3,4-thiadiazole hydrochloride
   Yield: 42% Melting point 199°–201° C.
13. 2-Amino-5-[3-(4-(2-nitrophenyl)piperazinyl)-Propyl]-1,3,4-thiadiazole hydrochloride
   Yield: 19% Melting point 154°–155° C.
14. 2-Amino-5-[4-(4-phenylpiperazinyl)butyl]-1,3,4thiadiazole hydrochloride
   Yield: 23% Melting point 244°–245° C.
15. 2-Amino-5-[2-(4-(2-nitrophenyl)piperazinyl)ethyl]-1,3,4-thiadiazole dihydrochloride
   Yield: 23% Melting point 196° C.
16. 2-Amino-5-[2-(4-(3-trifluoromethylphenyl)-piperazinyl)ethyl]-1,3,4-thiadiazole trihydrochloride
   Yield: 17% Melting point 180° C.
17. 2-Amino-5- [2- ( 4- ( 2-cyanophenyl)piperazinyl)ethyl ]-1,3,4-thiadiazole dihydrochloride
   Yield: 24% Melting point 181° C. (decomposition)
18. 2-Amino-5-[4-(1,2,3,6-tetrahydro-4-phenyl-pyridinyl)-butyl]-1,3,4-thiadiazole
   Yield: 22% Melting point 204°–205° C.
19. 2-Amino-5-[5-(1,2,3,6-tetrahydro-4-phenyl-pyrimidinyl)pentyl]-1,3,4-thiadiazole fumarate
   Yield: 26% Melting point 163°–165° C.
20. 2-Amino-5- [3-(4-pyridin-2-ylpiperazinyl)propyl]-1,3,4-thiadiazole
   Yield: 43% Melting point 195°–197° C.
21. 2-Amino-5-[4-(4-pyridin-2-ylpiperazinyl)butyl]-1,3,4-thiadiazole
   Yield: 32% Melting point 170°–171° C.
22. 2-Amino-5-[3-(4-pyrimidin-2-ylpiperazinyl)propyl]-1,3,4-thiadiazole
   Yield: 33% Melting point 183°–184° C.
23. 2-Amino-5-[4-(4-pyrimidin-2-ylpiperazinyl)butyl]-1,3,4-thiadiazole
   Yield: 25% Melting point 192° C.
24. 2-Amino-5-[2-(4-phenylpiperidinyl)ethyl]-1,3,4-thiadiazole
   Yield: 36% Melting point 187°–188° C.

SYNTHESIS OF THE STARTING MATERIALS OF THE FORMULA II a. 2-Amino-5-(2-chloroethyl)-1,3,4-thiadiazole:
   65 g of thiosemicarbazide were added a little at a time to 65 g of β-chloropropionic acid in 240 ml of concentrated sulfuric acid, during which the temperature of the mixture rose to 70°–80° C. The mixture was then refluxed for 1 h, cooled and poured into ice-water (500 ml). The mixture was neutralized with ammonia, and the precipitated product was filtered off with suction, washed with water and dried under reduced pressure.
   Yield: 56 g (57%) Melting point 133°–137° C.
   The following were prepared in a similar way:
b. 2-Amino-5-(3-chloropropyl)-1,3,4-thiadiazole
   Melting point 142°–145° C.
c. 2-Amino-5-(4-chlorobutyl)-1,3,4-thiadiazole
   Melting point 204°–205° C.
d. 2-Amino-5-(5-bromopentyl)-1,3,4-thiadiazole
   Melting point 118°–120° C.

Examples of pharmaceutical forms:

A) Tablets of the following composition are made in a tableting machine in a conventional way.

40 mg of substance of Example 1
120 mg of corn starch
13.5 mg of gelatin
45 mg of lactose
2.25 mg of Aerosil (chemically pure silica in submicroscopically fine distribution)
6.75 mg of potato starch (as 6% paste)
B) 20 mg of substance of Example 4
60 mg of core composition
60 mg of coating composition The core composition comprises 9 parts of corn starch, 3 parts of lactose and 1 part of 60:40 vinylpyrrolidone/-vinyl acetate copolymer. The coating composition comprises 5 parts of sucrose, 2 parts of corn starch, 2 parts of calcium carbonate and 1 part of talc. The coated tablets produced in this way are subsequently provided with an enteric coating.

C) 10 g of substance of Example 2 are dissolved in 5000 ml of water with the addition of NaCl and adjusted to pH 6.0 with 0.1N NaOH to produce a solution isotonic with blood. 1 ml portions of this solution are introduced into ampoules and sterilized.

We claim:
1. An aminoalkyl-substituted 2-amino-1,3,4-thiadiazole derivative of the formula I

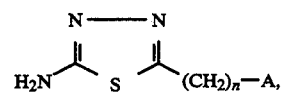

where
n is an integer from 2 to 6, and
A is

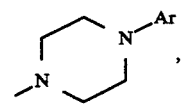

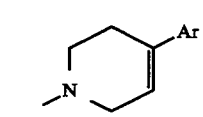

or

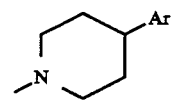

where Ar is phenyl which is unsubstituted or monosubstituted by $C_1$–$C_5$-alkyl, $C_1$–$C_5$-alkoxy, halogen, nitro, hydroxyl, trifluoromethyl or cyano, or is pyridyl, pyrimidinyl or thienyl, and the salts thereof with physiologically tolerated acids.

2. An aminoalkyl-substituted 2-amino-1,3,4-thiadiazole derivative of the formula I as claimed in claim 1, where n is 2,3 or 4 and A in the formula I is

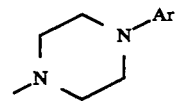

where Ar is unsubstituted phenyl, pyridyl or pyrimidinyl.

3. An aminoalkyl-substituted 2-amino-1,3,4-thiadiazole derivative of the formula I as claimed in claim 1, where n is 2,3 or 4 and A in the formula I is

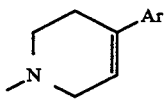

where Ar is unsubstituted phenyl, pyridyl or pyrimidinyl.

4. A pharmaceutical composition for treating disorders of the central nervous system or disorders associated with elevated blood pressure, which comprises an amino-alkyl-substituted 2-amino-1,3,4-thiadiazole derivative of the formula I as defined in claim 1.

5. A method for controlling diseases of the central nervous system or diseases associated with elevated blood pressure which comprises administering to a patient in need thereof a disease controlling effective amount of an amino-alkyl-substituted 2-amino -1,3,4-thiadiazole derivative of the formula I as defined in claim 1.

* * * * *